US00PP15527P2

(12) United States Plant Patent
Bessho et al.

(10) Patent No.: US PP15,527 P2
(45) Date of Patent: Feb. 1, 2005

(54) ***CALIBRACHOA* PLANT NAMED 'KAKEGAWA S63'**

(50) Latin Name: *Calibrachoa species*
Varietal Denomination: Kakegawa S63

(75) Inventors: Masao Bessho, Kakegawa (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 5 days.

(21) Appl. No.: 10/801,909
(22) Filed: Mar. 16, 2004
(51) Int. Cl.[7] ..... A01H 5/00
(52) U.S. Cl. ..... Plt./263
(58) Field of Search ..... Plt./263, 356

*Primary Examiner*—Kent Bell
(74) *Attorney, Agent, or Firm*—Jondle & Associates P.C.

(57) ABSTRACT

'Kakegawa S63' is a new variety of *Calibrachoa* plant. This new variety has red-purple petal lobes with purple petal lobe veins and dark green foliage.

1 Drawing Sheet

Genus/species: *Calibrachoa* species.
Varietal denomination: 'Kakegawa S63'.

BACKGROUND OF THE INVENTION

'Kakegawa S63' originated from a hybridization made in November 1998 in Kakegawa, Japan. The female parent was a *Calibrachoa* breeding line with a deep blue flower color and mounding habit known as 8B-48 (not patented). The male parent was a *Calibrachoa* breeding line with deep rose colored flowers and mounding habit and short internode length known as 97-1176 (not patented).

In February 1999, $F_1$ seed from this cross was sown and later transplanted outdoors. The $F_1$ plants were rose, magenta or blue in flower color and ranged from semi-creeping to compact in habit. Three, single-plant selections were made from the $F_1$ generation and vegetatively propagated. In February 2002, these selections were evaluated in 9 cm hanging pots in a greenhouse as well as in an open field. One selection was chosen based on the trial.

The selection was further evaluated from new vegetative plants in Salinas, Calif. during 2003. The selection was subsequently named 'Kakegawa S63' 'Kakegawa S63' was asexually reproduced by stem cuttings in Salinas, Calif. and was determined to reproduce true to type in successive generations of asexual propagation.

DESCRIPTION OF PHOTOGRAPH

This new *Calibrachoa* plant is illustrated by the accompanying photograph which shows blooms and foliage of the plant in full color. The colors shown being as true as can be reasonably obtained by conventional photographic procedures.

DESCRIPTION OF THE GENUS *CALIBRACHOA LLAVE & LEX*

Figure 1:
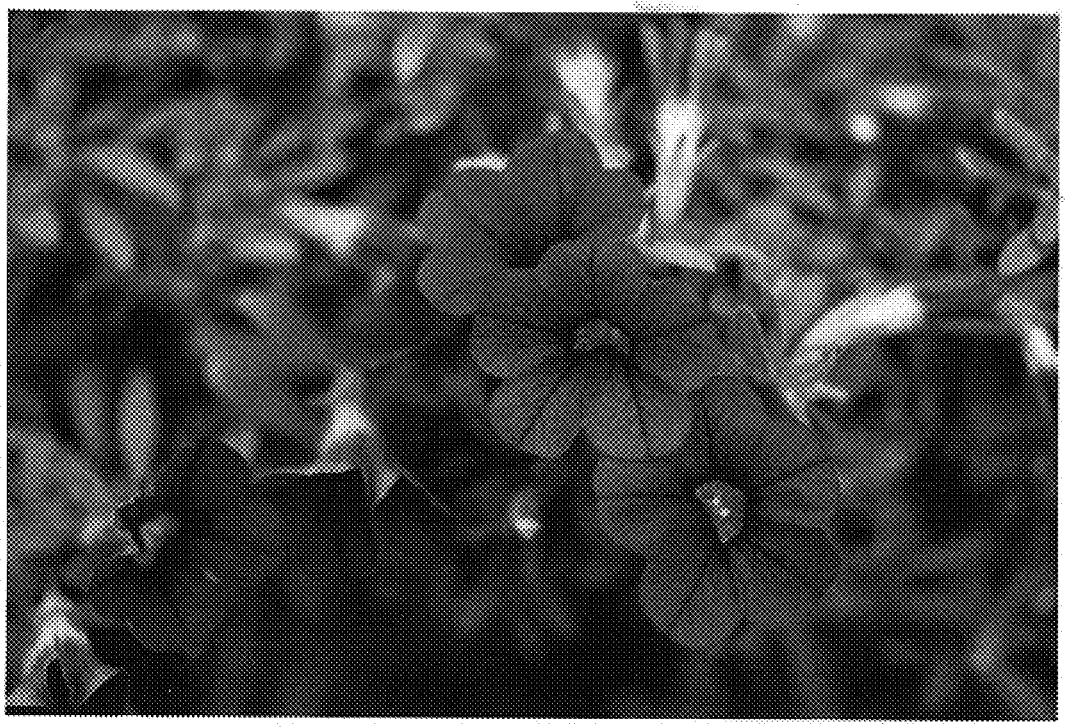
FIG. 1 shows a close-up view of flowers.
Figure 2:
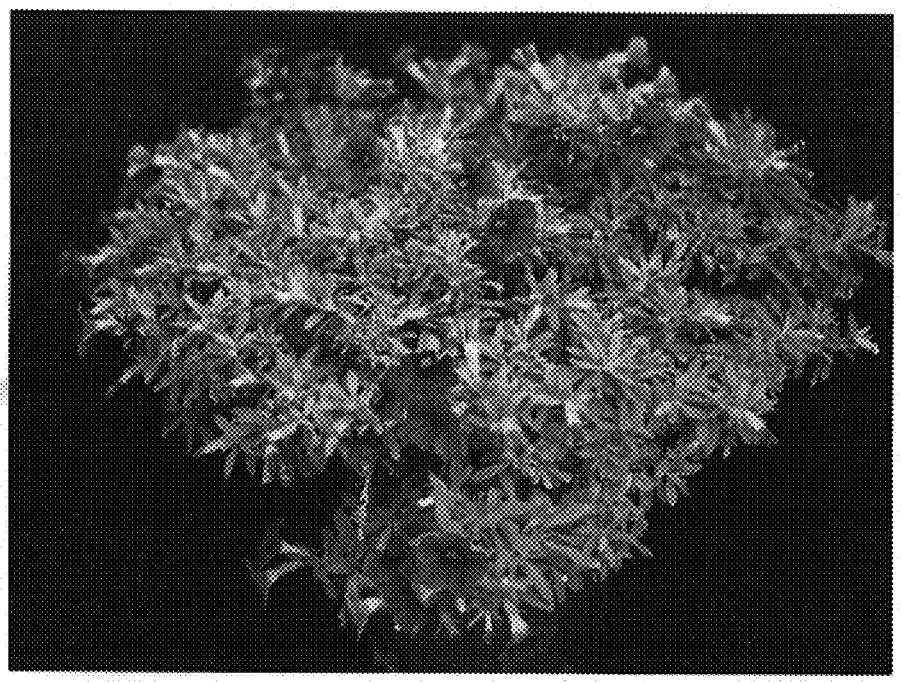
FIG. 2 shows the entire plant.

The genus *Petunia* was originally established in 1803 by A. L. Jussieu, who described both *P. parviflora* and *P. nyctaginiflora* as type species. Using a non-horticultural system that selected the first mentioned species as the type species (*lectotype*), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990, Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently, a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, a single outermost petal covers the other four, radially folded and terminally contorted petals. *Calibrachoa* flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 DIP 'N GROW: 9 water) root-inducing solution immediately prior to sticking into the cell trays. Cuttings were stuck into plastic cell trays having 98 cells and containing a moistened peat moss-based growing medium. The cuttings were misted with water from overhead for 10 seconds every 30 minutes until sufficient roots were formed.

Rooted cuttings were transplanted and grown in 20.0 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

DETAILED DESCRIPTION OF THE NEW PLANT

Data below collected on plants four months from rooted cutting and transplanted into 20.0 cm diameter pots. Color references are to the R.H.S. Colour Chart of The Royal Horticultural Society of London (R.H.S.). The following traits and characteristics describe the new variety.

Classification:
- *Family.*—*Solanaceae.*
- *Species.*—*Calibrachoa* sp.
- *Common names.*—*Calibrachoa.*

Parentage:
- *Female parent.*—Breeding line 8B-48 (not patented).
- *Male parent.*—Breeding line 97-1176 (not patented).

Growth:
- *Habit.*—Decumbent.
- *Height.*—13.0–15.0 cm.
- *Spread.*—40.0–45.0 cm for one plant when grown in a 20.0 cm diameter pot.
- *Life cycle.*—Perennial.
- *Form.*—Branching, dense, compact (shorter internode lengths).
- *Time to produce a rooted cutting.*—6 weeks.
- *Time to bloom from propagation.*—10 weeks.
- *Flowering requirements.*—Will flower so long as day length is greater than 12 hours and temperatures exceed 13° C.
- *Resistance/susceptibility.*—Excellent resistance to rain, heat and drought. Will not tolerate temperature below 10° C. Plants are susceptible to Botrytis, powdery mildew, various stem and root rots and certain viruses, like Tobacco Mosaic Virus and Impatiens Necrotic Spotted Virus. Plants can be infested with aphids, leafminer, whitefly and various Lepidoptera.

Stems:
- *Stem color.*—RHS 144B (yellow-green).
- *Anthocyanin color.*—RHS N77A (purple).
- *Pubescence.*—Heavy.
- *Pubescence color.*—Whitish.
- *Stem description.*—Round.
- *Stem length.*—1.5 cm–2.0 cm.
- *Stem diameter.*—1.8–2.1 mm.
- *Internode length.*—0.5–1.0 cm.

Leaves:
- *Leaf arrangement.*—Alternate.
- *Leaf shape.*—Elliptical.
- *Leaf tip.*—Mucronate.
- *Leaf base.*—Decurrent.
- *Leaf margin.*—Entire.
- *Leaf surface.*—Rough, dull.
- *Leaf length.*—2.3–2.7 cm.
- *Leaf width.*—0.7–1.0 cm.
- *Leaf color.*—Upper: RHS 137A (green); Lower: RHS 138B (green).
- *Leaf surface pubescence.*—Slight.
- *Leaf surface pubescence color.*—RHS N155B (white).
- *Petiole length.*—2.0 mm.
- *Petiole color.*—RHS 138B (green).
- *Venation.*—Pinnate.

Flowers:
- *Inflorescence type.*—Solitary.
- *Flowering habit.*—Indeterminate.
- *Duration of flower life.*—5 days.
- *Shape.*—The flowers are funnel shaped with five fissures.
- *Flower depth.*—2.0 cm–2.5 cm.
- *Floral tube length.*—1.3 cm–1.5 cm.
- *Floral tube diameter.*—0.4 cm–0.5 cm.
- *Flower diameter.*—2.5–3.0 cm.
- *Calyx.*—5 sepals, free.
- *Sepal shape.*—Lanceolate.
- *Sepal apex.*—Mucronate.
- *Sepal margin.*—Entire.
- *Sepal color.*—RHS 143A (green).
- *Bud shape.*—Ovate.
- *Bud length.*—1.5 cm.
- *Bud diameter.*—0.3 cm–0.4 cm.
- *Bud surface.*—Pubescent.
- *Bud color.*—RHS 8D (yellow).
- *Peduncle length.*—0.7–1.1 cm.
- *Peduncle color.*—RHS 144C (yellow green).
- *Ovary.*—Superior.
- *Pistil number.*—1.
- *Stigma color.*—RHS 150C (yellow).
- *Style color.*—RHS 149B (yellow-green).
- *Corolla.*—5 petals, fused.
- *Petal shape.*—Spatulate.
- *Petal apex.*—Truncate.
- *Petal margin.*—Entire.
- *Petal pubescence.*—Glabrous.
- *Petal size.*—0.6–0.7 cm×0.9–1.0 cm.
- *Petal color.*—Lobes: upper RHS N74A (red-purple) with RHS 79C (purple) veins; lower RHS 77A (purple) with RHS 79C (purple) veins; Corolla tube: inner RHS 2A (yellow) with RHS 79C (purple) veins; outer RHS 2B (yellow) with RHS 79C (purple) veins.
- *Stamen number.*—5, free.
- *Stamen color.*—RHS 150C (yellow-green).
- *Pollen color.*—RHS 8B (yellow).
- *Fragrance.*—Absent.
- *Seed production.*—None.

COMPARISON WITH MOST SIMILAR VARIETY

'Kakegawa S63' is a distinct variety of *Calibrachoa* owing to its short internode lengths, which lead to a compact growth habit, and purple petal lobe veins. 'Kakegawa S63' is most similar to the variety, 'Colorburst Rose' (U.S. Plant Pat. No. 12,147); however, there are differences as shown in Table 1 below.

TABLE 1

| | 'Kakegawa S63' | 'Colorburst Rose' |
|---|---|---|
| Internode Length | 0.5–1.0 cm | 1.5–2.0 cm |
| Petal Color Upper | Upper petal color is RHS N74A (red-purple) with veins of RHS 79C (purple) and an inner corolla tube of RHS 2A (yellow). | Upper petal color is RHS 74B (red-purple) with veins of RHS 202A (black) and purple tinge. |

Some differences between 'Kakegawa S63' and its parental lines are shown in Table 2 below.

TABLE 2

| Characteristic | 'Kakegawa S63' | Male (97-1176) | Female (8B-48) |
|---|---|---|---|
| Petal Color Upper | RHS N74A (red-purple) | Deep rose | Deep blue |
| Habit | Decumbent | Mounding | Mounding |
| Internode Length | 0.5–1.0 cm | 0.5–1.0 cm | 1.0–1.7 cm |

What is claimed is:

1. A new and distinct cultivar of *Calibrachoa* plant as shown and described herein.

* * * * *